US006775583B2

(12) United States Patent
Slodowski et al.

(10) Patent No.: US 6,775,583 B2
(45) Date of Patent: Aug. 10, 2004

(54) METHOD AND APPARATUS FOR USER GUIDANCE IN OPTICAL INSPECTION AND MEASUREMENT OF THIN FILMS AND SUBSTRATES, AND SOFTWARE THEREFORE

(75) Inventors: Matthias Slodowski, Jena (DE); Karl-Heinz Irmer, Jena (DE)

(73) Assignee: Leica Microsystems Jena GmbH, Jena (DE)

( * ) Notice: Subject to any disclaimer, the term of this patent is extended or adjusted under 35 U.S.C. 154(b) by 471 days.

(21) Appl. No.: 09/900,457

(22) Filed: Jul. 9, 2001

(65) Prior Publication Data

US 2002/0024663 A1 Feb. 28, 2002

Related U.S. Application Data

(60) Provisional application No. 60/216,688, filed on Jul. 7, 2000.

(51) Int. Cl.[7] .................................................. G06F 19/00

(52) U.S. Cl. ........................... 700/121; 700/108; 716/4; 356/256; 438/14

(58) Field of Search .............................. 700/90, 95, 97, 700/121, 108; 716/4; 714/25; 356/256; 438/14; 257/E21.521

(56) References Cited

U.S. PATENT DOCUMENTS

| 5,963,314 A | * | 10/1999 | Worster et al. .......... 356/237.2 |
| 6,388,747 B2 | * | 5/2002 | Nara et al. .................. 356/394 |
| 6,424,876 B1 | * | 7/2002 | Cusson et al. .............. 700/108 |
| 6,597,381 B1 | * | 7/2003 | Eskridge et al. ............ 345/804 |

* cited by examiner

Primary Examiner—Jayprakash N. Gandhi
(74) Attorney, Agent, or Firm—Crowell & Moring LLP

(57) ABSTRACT

A method, apparatus, and software for guiding users during optical inspection and measurement of coated and noncoated substrates with an optical measurement system is provided. The optical measurement system incorporates an integrated recipe and data browser with sortable features to facilitate the optical inspection and measurement by the user.

19 Claims, 23 Drawing Sheets

The Job

Job-Browser (Engineer Access)

Job-Browser (Operator Access)

View Data Details

The Job

Job Commander (Recipe Editor) - Cassette

Job Commander (Recipe Editor) - Sites - Patterned Wafer - Learn Wizard

Job Commander (Recipe Editor) - Sites - Patterned Wafer - Learn Wizard

Job Commander (Recipe Editor) - Sites - Map

Job Commander (Recipe Editor) - Sites - Patterned Wafer

Job Commander (Recipe Editor) - Application

Research Measurement (Engineer Access)

Run Options

Data Commander - Single Job

Data Commander - Wafermap

Job Browser (Job Batches)

Fig. 23

Prior Art

|  | THICKNESS MEASUREMENT PROGRAM |
|---|---|
| <F1> up | |
| <F2> down | 20 => Material catalogue |
| <F4> HELP | Measurement parameter |
| | Spectral measurement with 1 nm intervalls |
| | Spectral measurement with 1/3 nm intervalls |
| | Single lambda measurement |
| <F9> back | |
| <F10> enter | Main menu |

METHOD AND APPARATUS FOR USER GUIDANCE IN OPTICAL INSPECTION AND MEASUREMENT OF THIN FILMS AND SUBSTRATES, AND SOFTWARE THEREFORE

REFERENCE TO PROVISIONAL APPLICATION

This application claims the benefit of prior filed co-pending provisional application Serial No. 60/216,688, filed on Jul. 7, 2000, pursuant to 35 U.S.C. §119(e).

BACKGROUND AND SUMMARY OF THE INVENTION

The invention relates to a method, an apparatus, and software for guiding users during optical inspection and measurement of coated and noncoated substrates.

In the semiconductor industry, a plurality of processing steps are required for producing integrated circuits. In this process, structures are applied on substrates, especially on silicon wafers, by means of diverse chemical and physical processes. In so doing, dust particles or defects on the substrate or on the structures are fatal to the success of the subsequent processing steps or for the subsequent functioning of the integrated circuit. The same also applies to inaccurate thicknesses or inaccurate optical parameters on the layers applied on the substrate and by means of which the structures are produced. Therefore, devices for detecting dust particles and defects and for measuring the layer thickness are mandatory for producing semiconductors. To this end, optical systems are especially appropriate for inspection, defect detection and layer analysis, since they work in a contactless and destruction free manner.

There exist a number of different optical inspection, defect and layer analysis systems in the state of the art and their use has been successful in the analysis of structured and non-structured wafers.

Such optical systems are used in particular in the production line of semiconductor manufacturers. They are fully automated. Pull-out arms remove a wafer from a wafer cassette and transport it under a microscope in order to inspect the wafer surface at the appropriate magnitude. The dust particles and defects are recognized visually or with a video or CCD camera and then analyzed. The layers applied on the wafer are measured on a very small measurement spot; and their visual material properties and thicknesses are found. With the aid of an automatically moveable table many points on the wafer can be inspected and measured. The user specifies the appropriate inspection and measurement programs.

In layer analysis systems, the visual material properties (primarily the refraction index n, absorption coefficient k, and the reflectivity) of the substrates and the layers, applied thereon, their thicknesses and layering are determined. These usually very thin layers are made of different substances, such as silicon dioxide, silicon nitride, aluminum or paint; and their thickness ranges from approx. 1 nm to more than 50 $\mu$m. The optical measurement is done with spectrophotometers and/or ellipsometers or spectroellipsometers. The measurement spot to be examined on the wafer is illuminated with light of different wavelengths, which can range from ultraviolet to infrared. The reflected light is measured and analyzed.

Since the goal in manufacturing wafers is to produce ever thinner layers and finer structures, the requirements on the accuracy of the optical measurement systems, with which the dimensional accuracy of the layers and structures can be proven, increases proportionally. In addition to the demand for increased accuracy, one must also consider the endeavor to increase the number of items produced. Thus, for example it is necessary in the continuous production of wafers to inspect and measure them at ever shorter time intervals and, if possible, online. In so doing, it is important that the optical measurement systems be user friendly and easy to operate.

The principle operating sequence consists of entering information in order to set up a measurement recipe (run parameters, run programs, measurement parameters), to perform the measurements and display the measurement results. The run programs determine, for example, the wafer handling, thus which wafer is taken from which cassette and at which coordinate points the wafer is supposed to be examined. The alignment of the wafer, in which the wafer is aligned with respect to the coordinate system of the optical measurement system, the depositing of the wafer on a motorized table and the moving of the wafer under the microscope are usually fully automatic.

Past optical inspection and measurement systems show, for example, one or more window(s) on a computer screen, where the run and measurement parameters to be set or the run and measurement programs are listed as key words. On the left hand edge of the list of key words there is a symbol, shown as an arrow, which moves in the vertical direction by means of the cursor keys of the computer keyboard and thus can be moved past the key words. If in this manner the arrow is positioned on a key word that indicates a parameter value, the parameter value can be entered. If the key word means a run or measurement program, it is executed by depressing the return key. To retrieve the preceding window or another window, the arrow is moved to the corresponding position and the return key is depressed. In addition, the function keys of the computer keyboard can be used for help functions. These known menu guidance procedures for entering measurement parameters and executing and displaying the results of measurement programs are time consuming and not very easy to survey.

The object of the invention is to provide a user guide for optical inspection and defect detection on the surfaces of substrates and/or layers applied thereon, and for optical measurement of substrates and layers, applied on the substrates, with a layer analysis system that is simple, easy to survey, and fast and easy to learn.

This problem is solved according to the invention with an integrated recipe and data browser. Other embodiments are apparent from the features described herein. In addition, interactive research measurements can also be executed during a recipe setup. In this respect, the set values found during optimal measurement can be incorporated into the current recipe.

The integrated recipe and data browser serves to set up the device settings and simultaneously display the data. The word "integrated" is used herein to express the simultaneousness of the display of the recipe and the data browser on the screen and the access to both browsers. The recipe and data browser can be divided in any way on the screen. Preferably, the data browser is arranged in a screen area below the recipe browser. This arrangement of the browser is the same for all basic operations, namely setting up measurement recipes, performing measurements, viewing results and also finding again measurements that have already been performed or earlier measurements. Thus, it is easy to learn, easy to handle and very comfortable for the user.

The user sets up the recipe, which is defined, among other things, as the selection of run and measurement programs, the input of measurement parameters, such as choice of lens, illumination, optionally the focus setting, camera setting, etc, but also the input of how the measured values shall be stored, whether they are to be compared with each other and which evaluation method shall be selected. Information data can also be entered, such as the lot number of the wafers or their diameter or who the operating engineer is and the like. Since a recipe must be regarded virtually as a job, the recipe browser is also called the job browser, as is the case below and in the figures.

If there already exist data sets from previous measurements, they can be viewed in the data browser, after they have been retrieved correspondingly in the recipe browser.

To further facilitate storage or search of data sets, the directories and the subdirectories arranged in tree structures (as is known from the WINDOWS® operating system) can also be shown in another field on the screen. Preferably, the "directory tree" is displayed in the left half of the screen. Thus, the user can retrieve directly the recipe and data sets, stored in a subdirectory; or he can store generated recipe and data sets in existing or newly generated subdirectories.

Thus, the entire browser—referred to as simply the browser in the following—is divided into three areas:

(1) Left area: "directories". Tree structure of the jobs stored in self-generating directories;
(2) Top right area: "Jobs of selected directory" shows the jobs of the selected directory; and
(3) Bottom right area: "Data of selected jobs" or equivalent "measurements of selected jobs" shows the measurements of selected jobs.

The size of the areas can be scaled arbitrarily by the operator.

In the areas "jobs of selected directory" and "measurements of selected jobs" the entries (lines) can be ordered according to specific criteria (columns). Columns of the job area are, for example: name, owner, scan type, layer stack, date of preparation, last change, etc. If one clicks a column heading, the content is ordered.

The advantages of the browser are, on the one hand, the easy selection of jobs by browsing in different content categories, according to which they can also be ordered. In the case of a few hundred jobs (measurement recipes), which are generated in a semiconductor plant, it is not only an obvious relief for both the operator and the engineer but also saves them time.

In addition, the selection of jobs is easier and it is possible to get a fast overview of the area "measurements of selected jobs", displayed for each job. Here, the averages of all data measured with this job are listed, since the prehistory of the job can be inspected. It is possible to evaluate immediately without any detours the current measurement results, even with respect to previously measured data.

Following startup of the software, the job browser starts as the main screen. At the very top of the screen there is a toolbar. With the backspace key on the left of the toolbar, one always gets back to the main screen.

Besides the job browser, there are also as the main modules from the user's point of view the job commander, which generates and edits the measurement and evaluation recipes (with "back" being back to the browser) and the data commander for evaluating data details, generating graphics, etc.

The job commander serves to generate and edit measurement and evaluation recipes and is the main working tool for the engineer.

The main contents of a recipe are organized on tab cards ("register cards"). One of the tab cards, the page "application", includes a "research" area. With the toolbar button "measure" a measurement can be performed, starting from any position of the job commander, at the current position with the current settings. The results and all of the important information (among other things, with the measurement spectrum) are displayed in the "research" area. Several such measurements can be stored in a research file and later reloaded. When browsing through the research measurements, the settings stored there are incorporated. The best setting can be incorporated into the current recipe.

The advantages of the job commander lie in the organization into tab pages and the interactive, storable and integratable research measurements from any position of the job commander. Thus, the engineer can easily find interactively the system settings that are best for the respective application. In addition, they can be stored and incorporated for subsequent repeat measurements or for the work of the operator on the production line.

Like the browser, the data commander is divided into several areas, which can also be freely scaled by the operator. In a top area "measurements of job: name" there is the same content as in the bottom area of the browser, namely the average values of the wafer measurements of the job. In the bottom area are the measurement points with respect to the wafer measurements, selected in the top area. On the right hand side of the screen are the operating elements that apply to the respective area.

The advantages of the data commander are the same "look and feel" as with the browser and the statistical data under each column.

Thus, the browser, the job commander and the data commander are designed for optimal user friendliness and easy and fast operation for complex optical inspection and measurement equipment, especially for the semiconductor industry. Besides the easy setup of measurement recipes and surveyable display of measurement results, the extreme flexibility of the modules also makes them suitable for fast adjustment to changing requirements.

Other objects, advantages and novel features of the present invention will become apparent from the following detailed description of the invention when considered in conjunction with the accompanying drawings.

BRIEF DESCRIPTION OF THE DRAWINGS

FIG. 23 depicts an example from the state of the art.

DETAILED DESCRIPTION OF THE DRAWINGS

Figure 1:
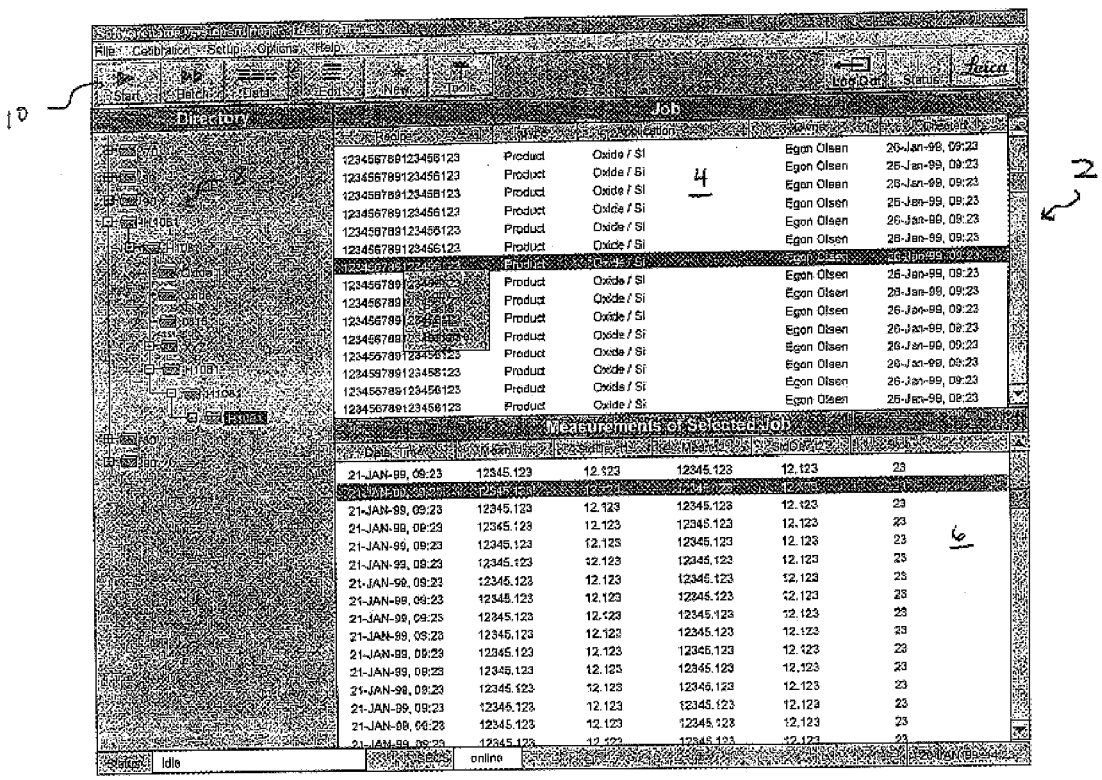
FIG. 1 is a schematic drawing of an integrated recipe and data browser and a directory tree.

In a start window 2 (main screen) of a display, FIG. 1 depicts the integrated recipe 4 and data 6 browser of the invention under "JOB" in a top field of the screen (i.e., the recipe) and under "Measurements of Selected Jobs" in a bottom field of the screen. In the recipe browser 4 one can see the jobs of the directory, just selected, on the individual lines. A line can be selected (highlighted line); and at the same time in accordance with the marked lines of the recipe browser the related data appears in the data browser 6 (highlighted line). By browsing through the recipe browser all jobs of the selected directory appear in the form of line-by-line information (recipe/job number, job type etc.) in the recipe browser. In an analogous manner the data, belonging to a selected line of the recipe browser, can also be browsed by the browser in the data browser. In both browsers the content can be ordered according to different criteria, e.g. according to job number, according to product, to owner, date of preparation, etc. The viewing areas of the browser can be arbitrarily set by the user.

In the left area of the screen the directory tree 8 ("directory tree") and the currently opened directory (highlighted) can be seen at the same time. The individual directories can be opened by clicking on the tree entries; and the corresponding information appears in the recipe 4 and data 6 browser. Even the field of the directory tree can be set arbitrarily. The screen content is set up and constructed with a graphical user interface (GUI).

At the top edge of the screen is a toolbar 10, with which, among other things, the recipe and data browser can be edited.

Figure 2:
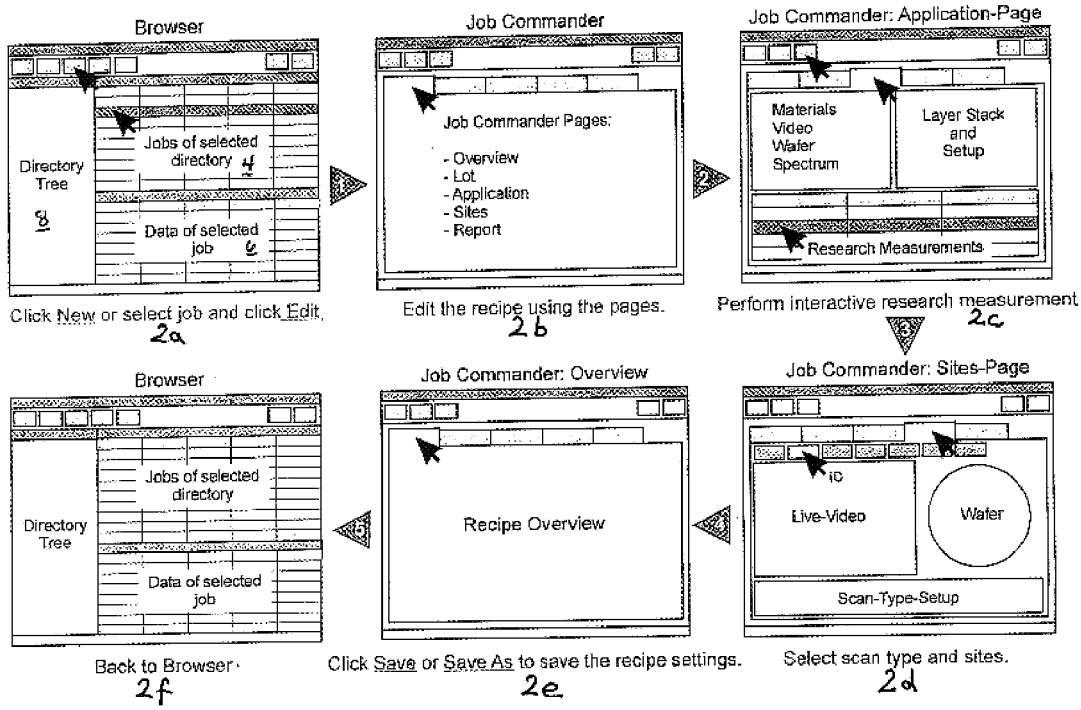
FIGS. 2a–2f schematically illustrate the run sequence of a recipe setup.

FIGS. 2a–2f depict one example for the run sequence of a recipe setup. In FIG. 2a, the integrated recipe 4 and data 6 browsers of the invention are shown in a top and bottom field of the screen as "jobs of selected directory" and "data of selected jobs". The left hand field shows the directory tree ("directory tree"). By clicking on the "new" or "edit" button on the toolbar 10 (see FIG. 1), a new job can be set up or a job, marked in the recipe browser, can be retrieved to change the content. The job commander then appears with register cards, as is apparent in FIG. 2b. The content of a recipe is entered on the corresponding register cards or changed. For example, material data, video parameters, wafer data and data about spectrums or the construction of layers can be incorporated on the register card "application" according to FIG. 2c. By actuating the "measurement" button on the toolbar, one or more measurement(s) is/are performed with the set parameters; and the measurement results are displayed in a bottom field on the screen ("research measurements").

The register card "sites" in FIG. 2d shows graphically the measurement position on the wafer. A cross hair on the wafer indicates the measurement position. At this measurement position a picture of the wafer surface is taken with a video camera, and the video picture is shown live in a left field of the screen. The optics (microscope) (not illustrated) of the optical measurement system deliver together with the video camera a correspondingly enlarged live image. Above the video image there is a button bar 10, with which different scan types can be selected. For example, individual or several defined points can be scanned on the wafer and examined. Or individual lines on the wafer or the entire wafer can be scanned. It is possible to start and execute a measurement run directly from this register card "sites", according to the type of scan setup. Of course, a measurement, for example a layer thickness measurement, can also be performed directly at the current location on the wafer, which is marked with the cross hair and of which a live video image is shown. The results are displayed immediately.

To further improve, if necessary, the measurement results, the setting parameters can be changed. These changes can be done manually or automatically. In this manner the user can arrive at optimal measurement results either specifically or by trial and error. The user's experience or specific characteristic values with respect to the quality of the evaluation or also direct data about the quality of the evaluation, delivered automatically by the measurement system (e.g. fit), decide whether a measurement result is optimal. The setting parameters for the diverse measurement results and in particular for a targeted optimal measurement result can be incorporated for the current recipe. Thus, an interactive, storable research measurement can be performed during a recipe setup. If desired, the current setting values can also be incorporated into the current recipe.

The register card in FIG. 2e gives an overview of all such setup recipes with the respective settings. All recipes or a part thereof, including the related measurement results, can be stored.

By clicking on the "back" button of the toolbar, the "browser" start screen appears again (FIG. 2f).

Figure 3:
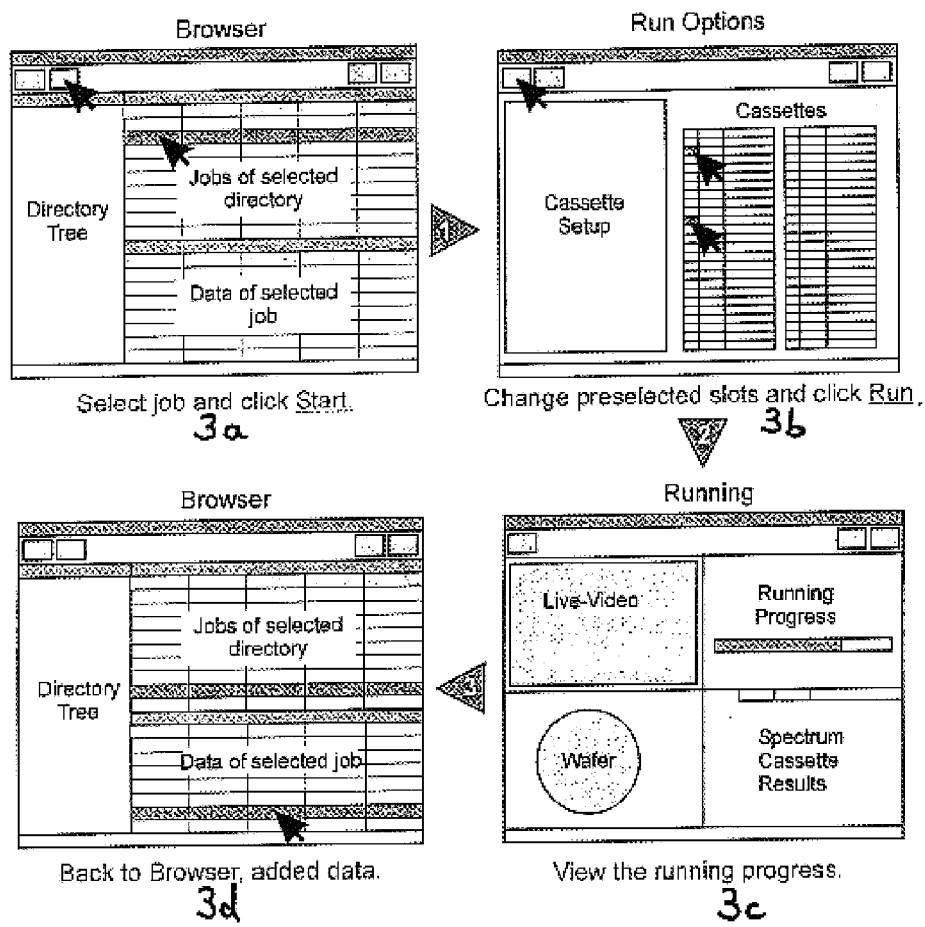
FIGS. 3a–3d schematically illustrate the sequence of an inspection or measurement run process.

FIGS. 3a–3d give an example of a flow sequence for a job run on the production line. The start screen is also the browser with the already described breakdown into recipe and data browser and the directory tree (FIG. 3a). First, the operator selects options for the inspection or measurement run, such as which wafer shall be taken from which cassette (FIG. 3b). During the measurement run, the current measurement position on the wafer, the related video image and information on the amount already processed (in %) of the measurement run are displayed on the screen (FIG. 3c). Thus, the measurement run can be watched and monitored. After the run, the browser appears again with the newly added data (FIG. 3d).

Figure 4:
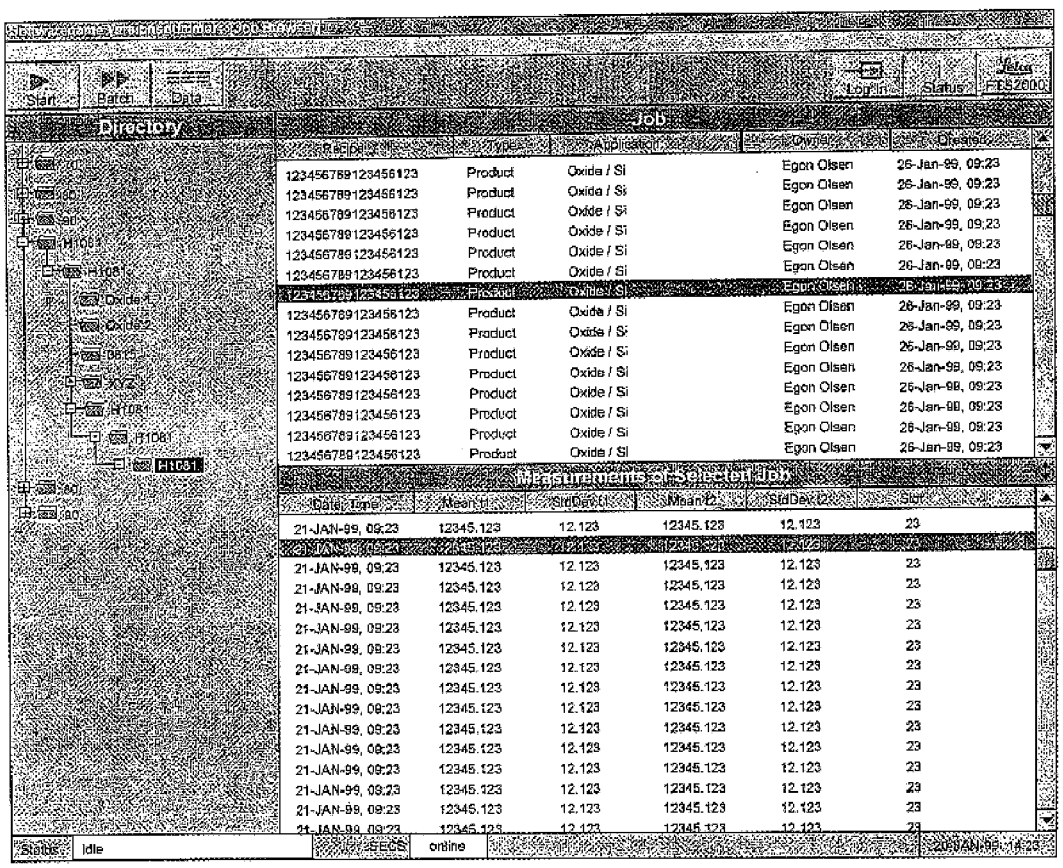
FIG. 4 is a schematic of the details of the browser during a measurement run.

FIG. 4 shows details of the browser during a measurement run.

To watch the generated data—or also older data—the desired job is selected, according to the sequence in FIGS. 5a–5e in the browser and activated by clicking on the "data" button (FIG. 5a) of the data commander (FIG. 5b). The data are displayed numerically. They can, if desired, be sorted in different ways. The data can also be displayed graphically, as depicted in FIG. 5c. In this case, the example is a layer thickness measurement over the entire wafer, for which the measured sites on the wafer and the related layer thicknesses are displayed with different symbols. In addition, the contours, thus the lines of identical layer thickness, are displayed. In the "graph control" menu, different parameters can be set for the graphical representation.

By actuating a "job summary graph" button (FIG. 5d), the measurement results can also be plotted over time. This is especially important in order to recognize the changes in the production process. Thus, for example, during the production runs, measurements are done automatically at a specific site coordinate on each wafer and this information is stored. In this manner conclusions about the production process over specific periods of time (hours, days, or weeks) can be drawn from the measurement curves. FIG. 5e shows such a measured value curve, e.g. changes in the layer thickness, as a function of time.

Figure 5:
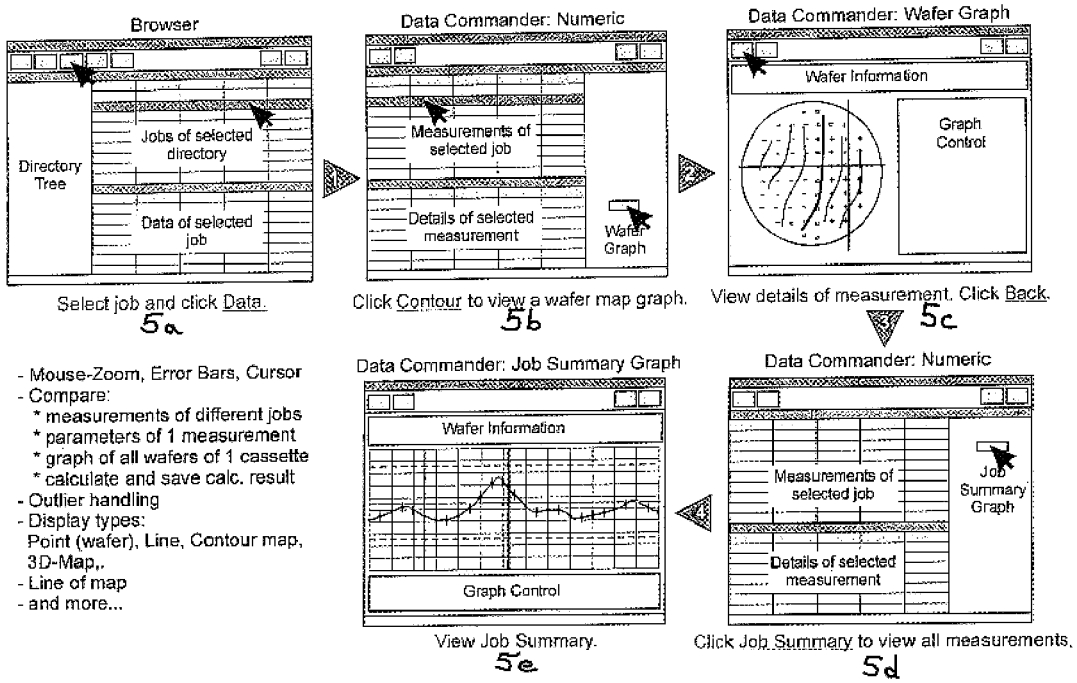
FIGS. 5a–5e schematically illustrate the run sequence with the data commander to display inspection and measurement results.

However, a plurality of other informative graphic representations can be displayed that are listed as key words on the left bottom in FIG. 5.

Figure 6:
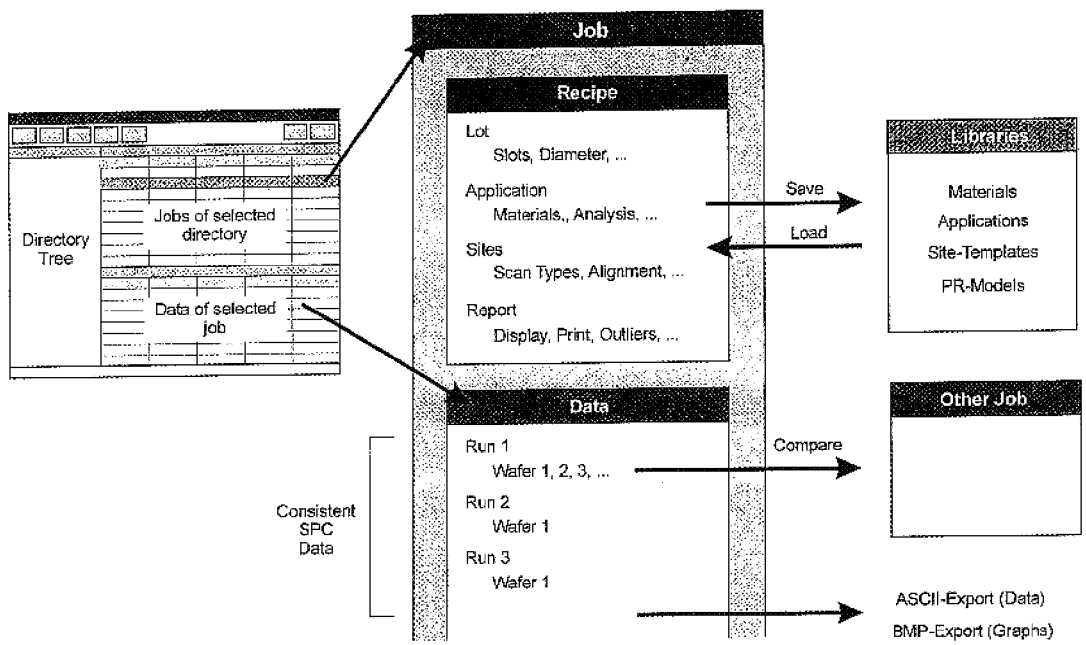
FIG. 6 is a schematic drawing of examples of the content of the recipe and data browser and the connections to the outside.

FIG. 6 provides an overview of the browser as the starting screen with access to some important setting parameters of the recipe browser and its exchange with the library and also access to the data of the data browser, whose data can be compared with each other or with older data ("other jobs") by means of SPC (static process control). The data can also be exported by ASCII code or in bit map format for use with other programs.

Figure 7:
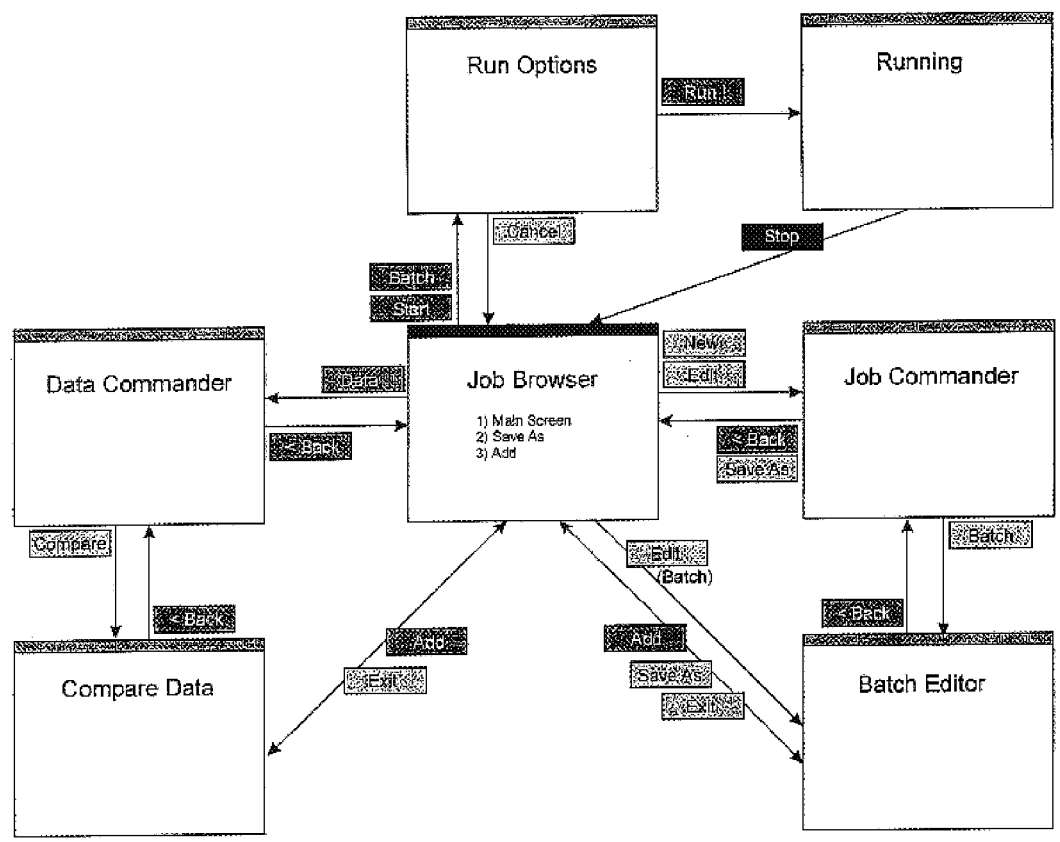
FIG. 7 is a schematic drawing of an overview of the relationship between the recipe and data browser ("job browser") and other browsers and programs.

FIG. 7 provides an overview of the relationship between the recipe and data browser (job browser") and various modules, especially the job commander, the data commander and the measurement run modules ("run options", "running").

Figure 8:
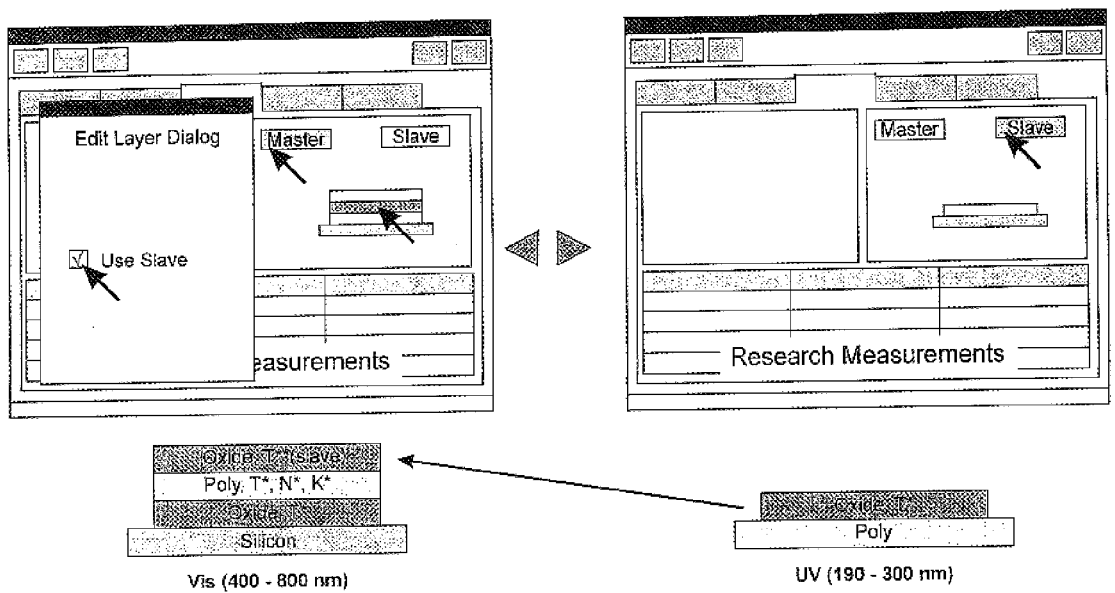
FIG. 8 is a schematic drawing of the use of two measurement applications.

FIG. 8 provides an example of a specific measurement application for measuring the layer thickness. With a master and a slave setting two different types of measurements can be combined. These types of measurements are, for example, the use of two different wavelength ranges for the optical measurement or the use of two different measurement methods, like spectrophotometry and ellipsometry or spectroellipsometry. The two types of measurements are combined in such a manner that the measurement result of one type of measurement serves as the preliminary information and flows into the measurement in the other type of measurement. Thus, for example, a layer stack of three layers on a silicon wafer (FIG. 8) can be measured first in the ultraviolet range. Since the average layer is made of UV impermeable polysilicon, only the uppermost layer is measured; and the layer thickness and optionally other optical parameters are determined. This measurement result is used to measure in the visible wavelength range, to which the polysilicon is permeable and thus all layers can be measured.

Figure 9:
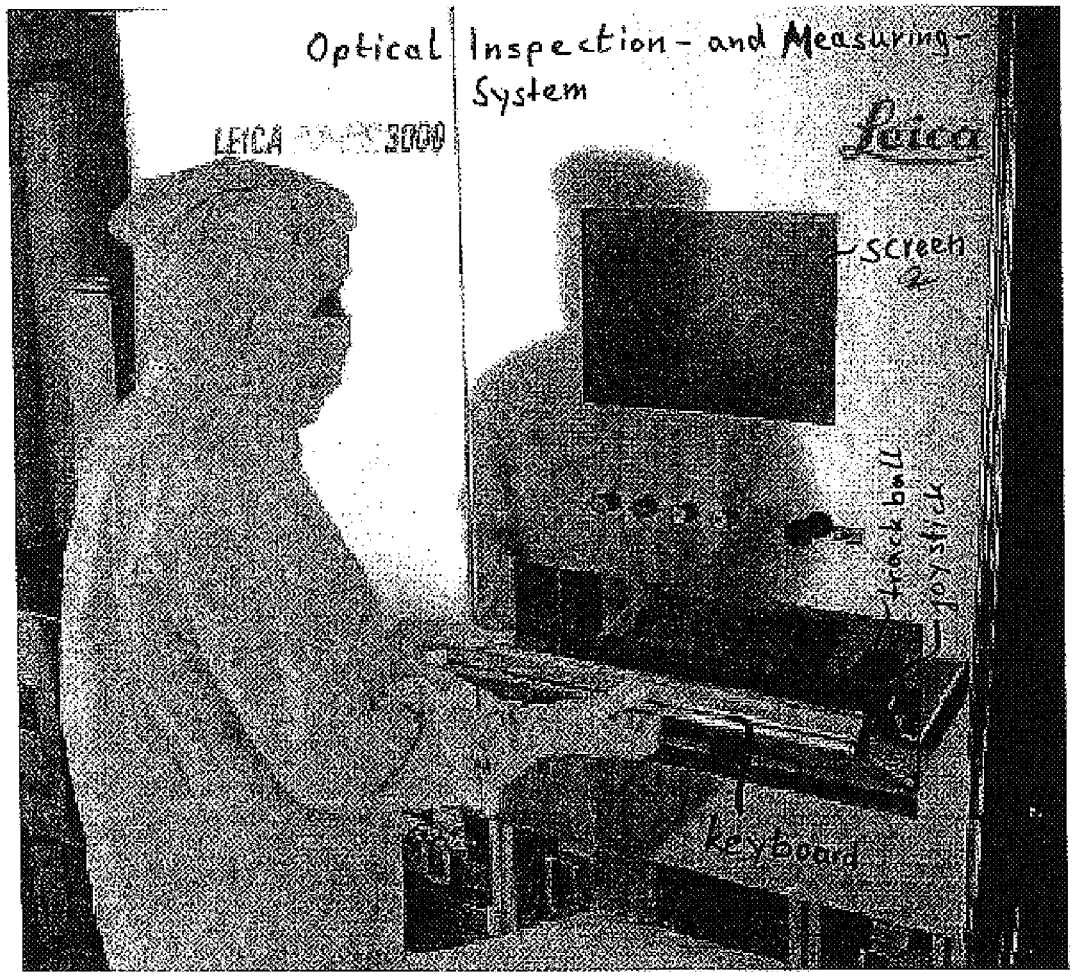
FIG. 9 is a picture of an optical measurement system with a screen for the browser of the invention.
Figure 10:
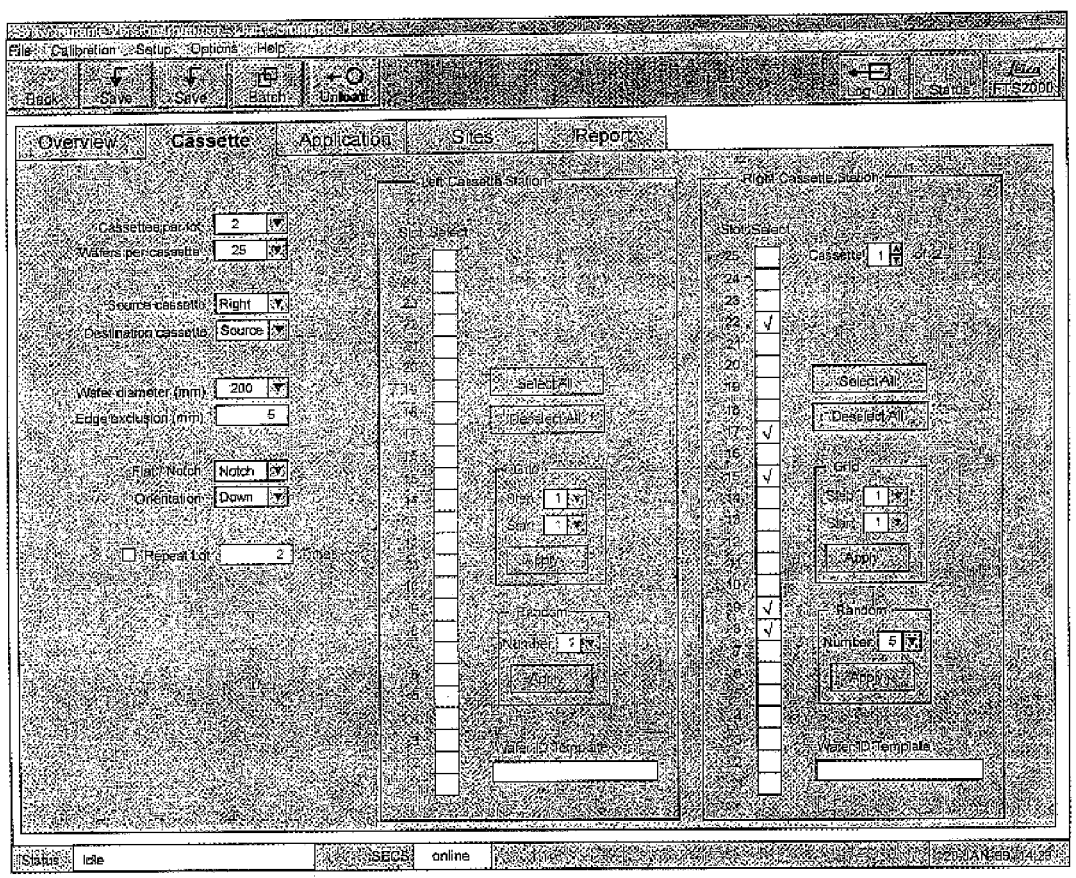
FIGS. 10 to 16 are schematic drawings of the details of the job commander.
Figure 11:
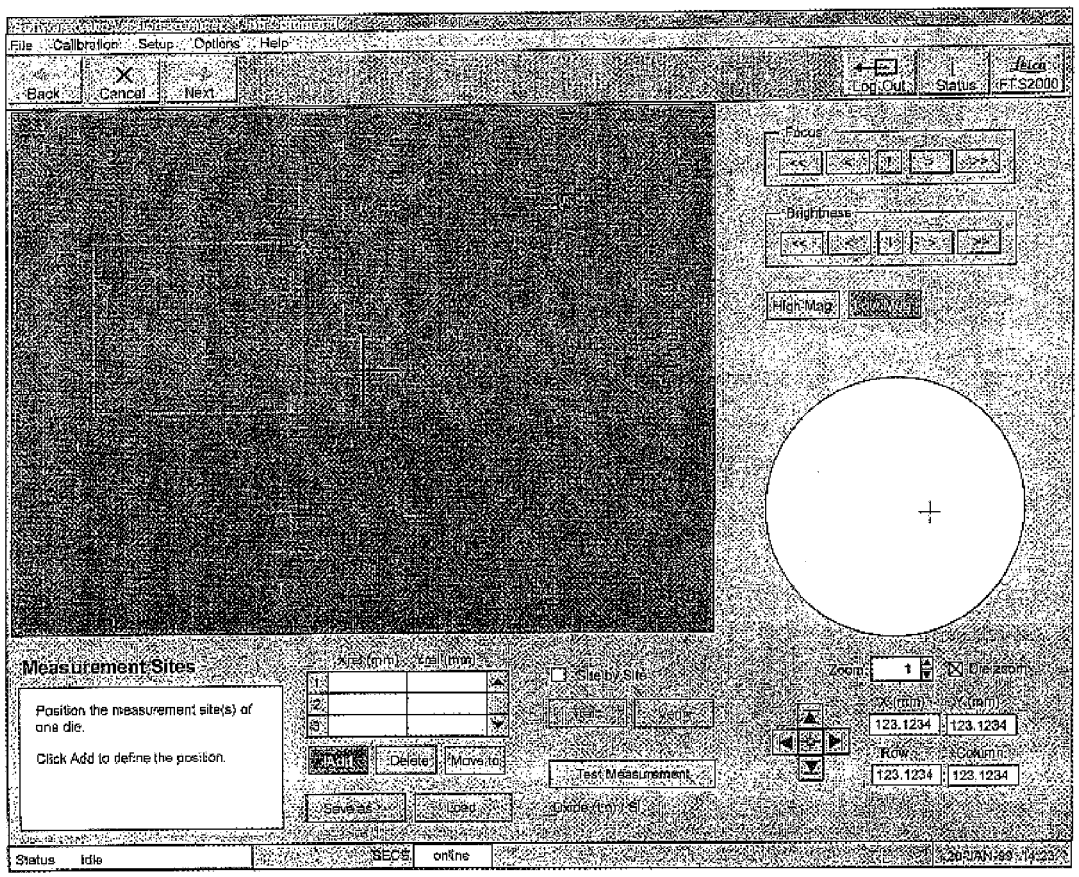
Figure 12:
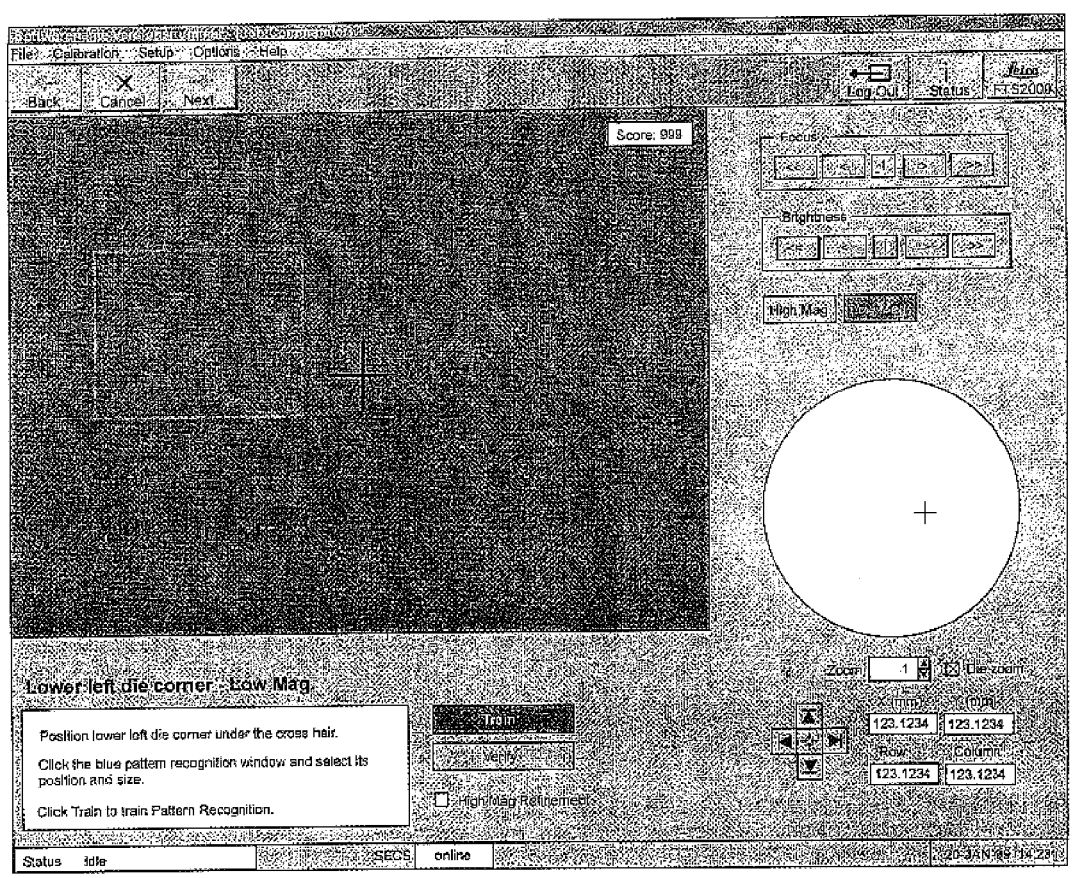
Figure 13:
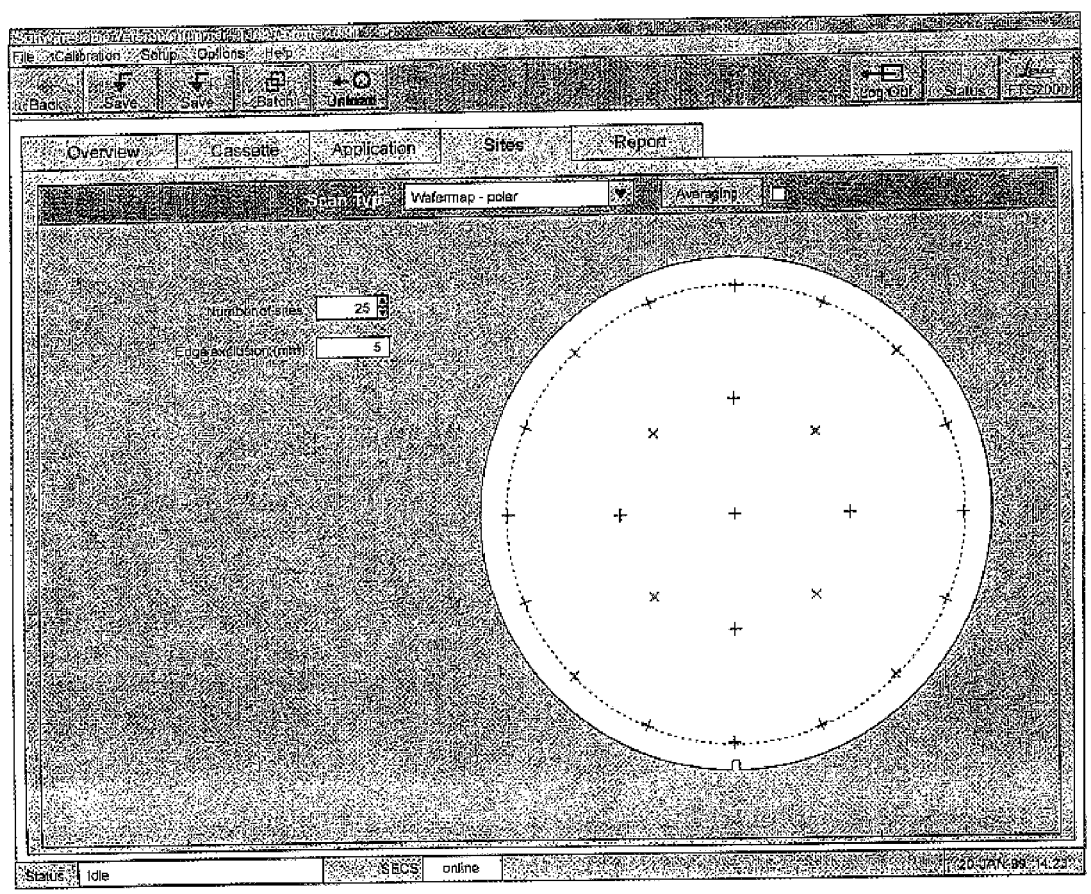
Figure 14:
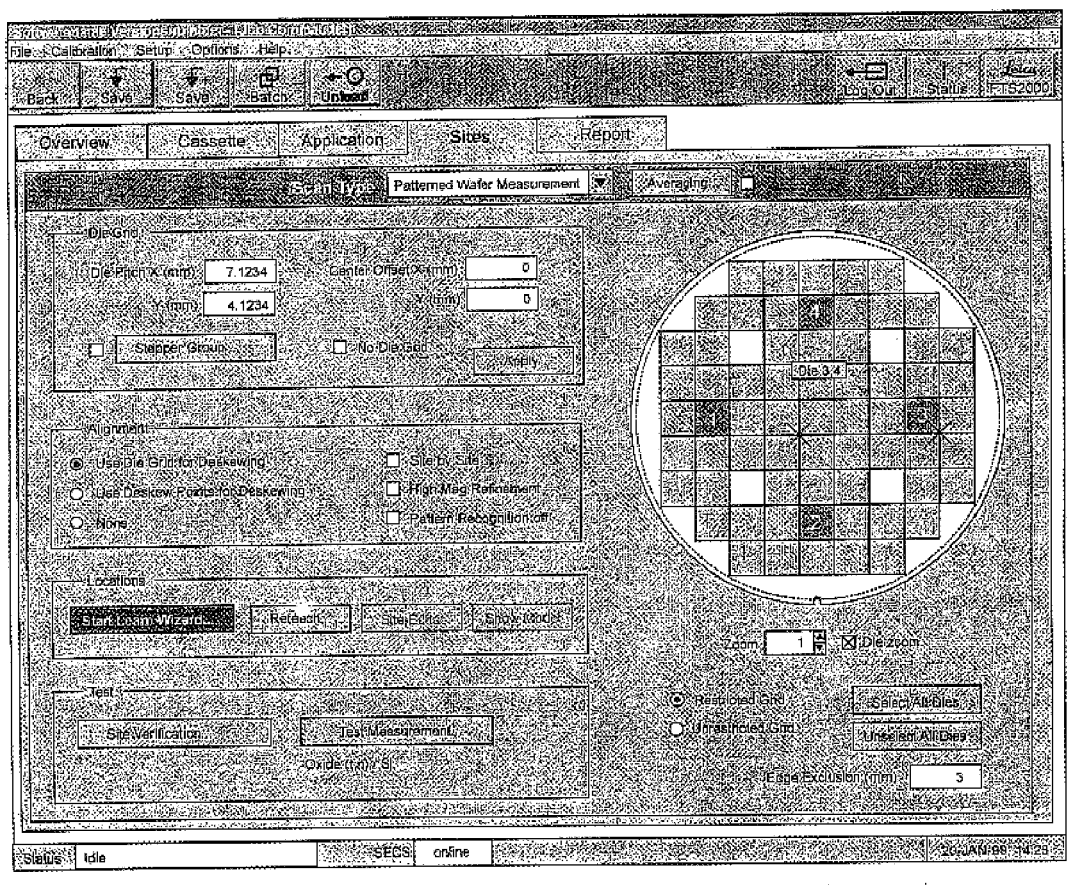
Figure 15:
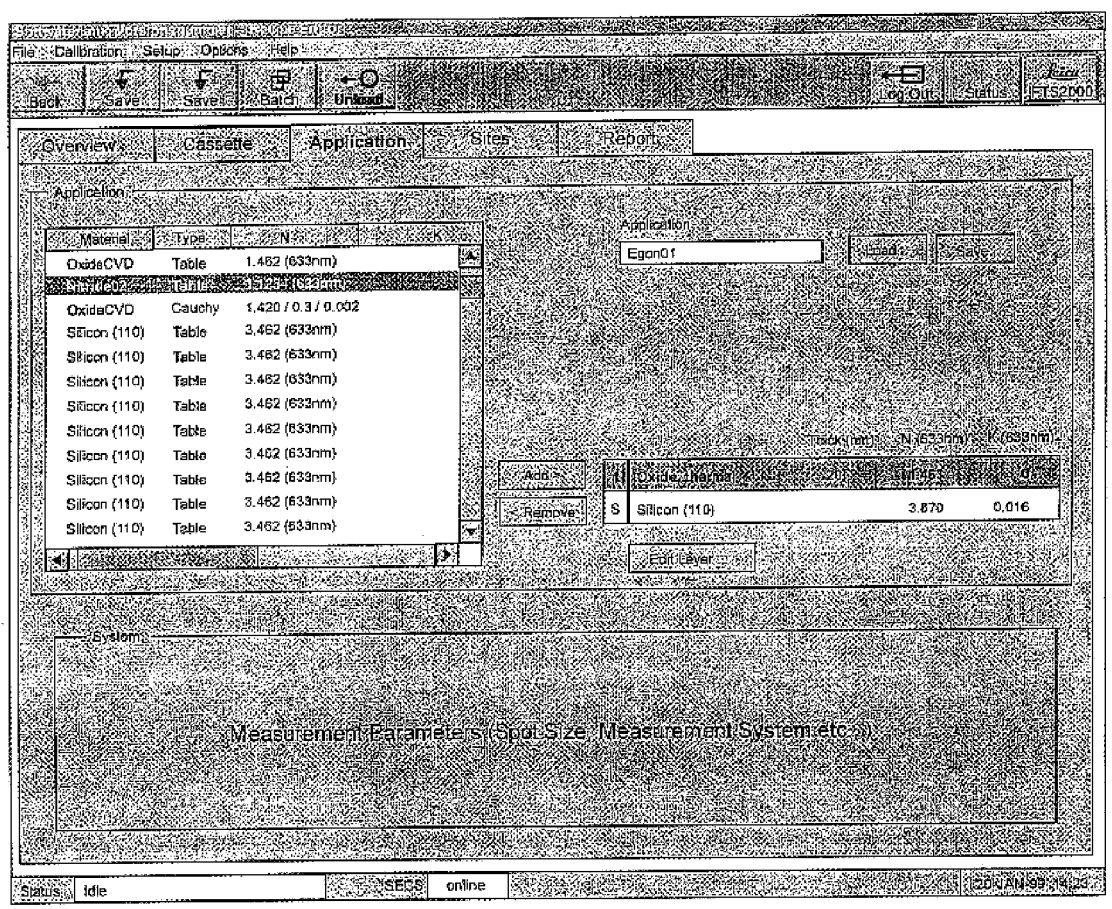
Figure 16:
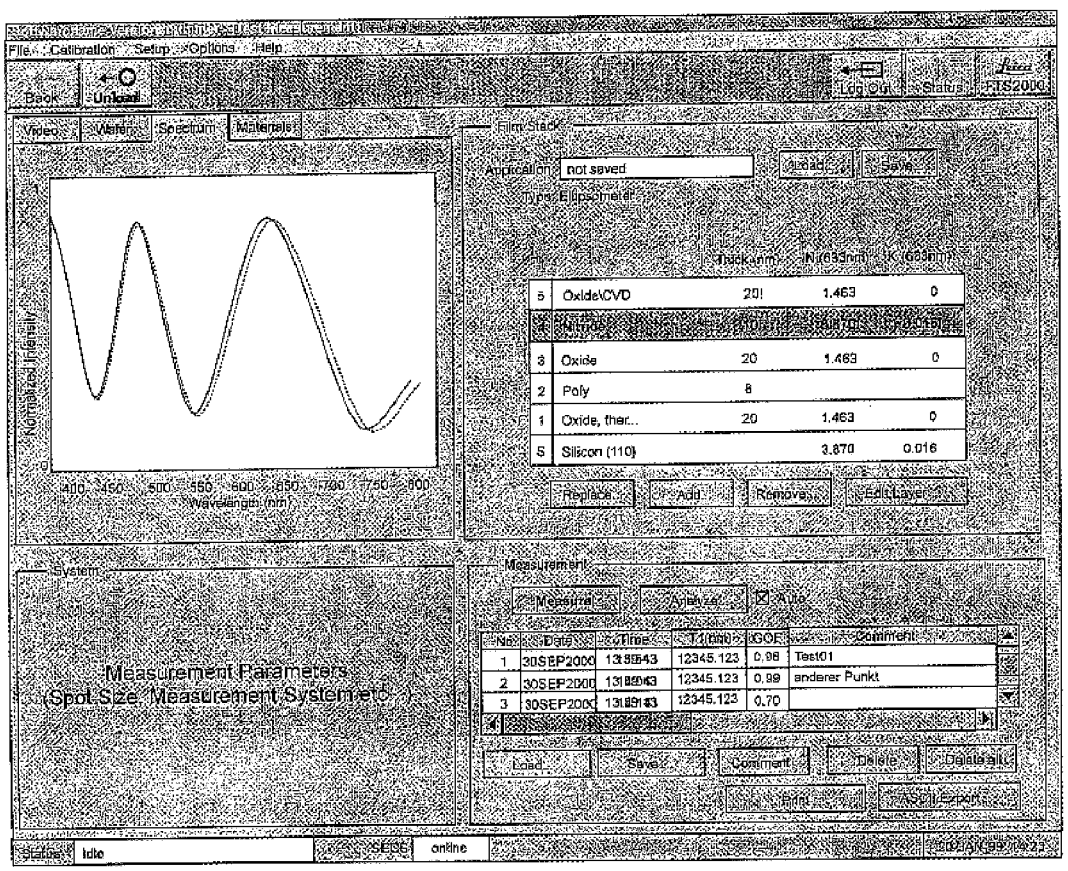

FIG. 9 provides as an example of an optical measurement system an overview of a layer analysis system. Approximately in the center of the measurement system a screen is shown. On this screen appear the windows, depicted in the other figures. A user can operate the measurement system by entering information via a keyboard, a joystick or a mouse or a trackball.

Figure 17:
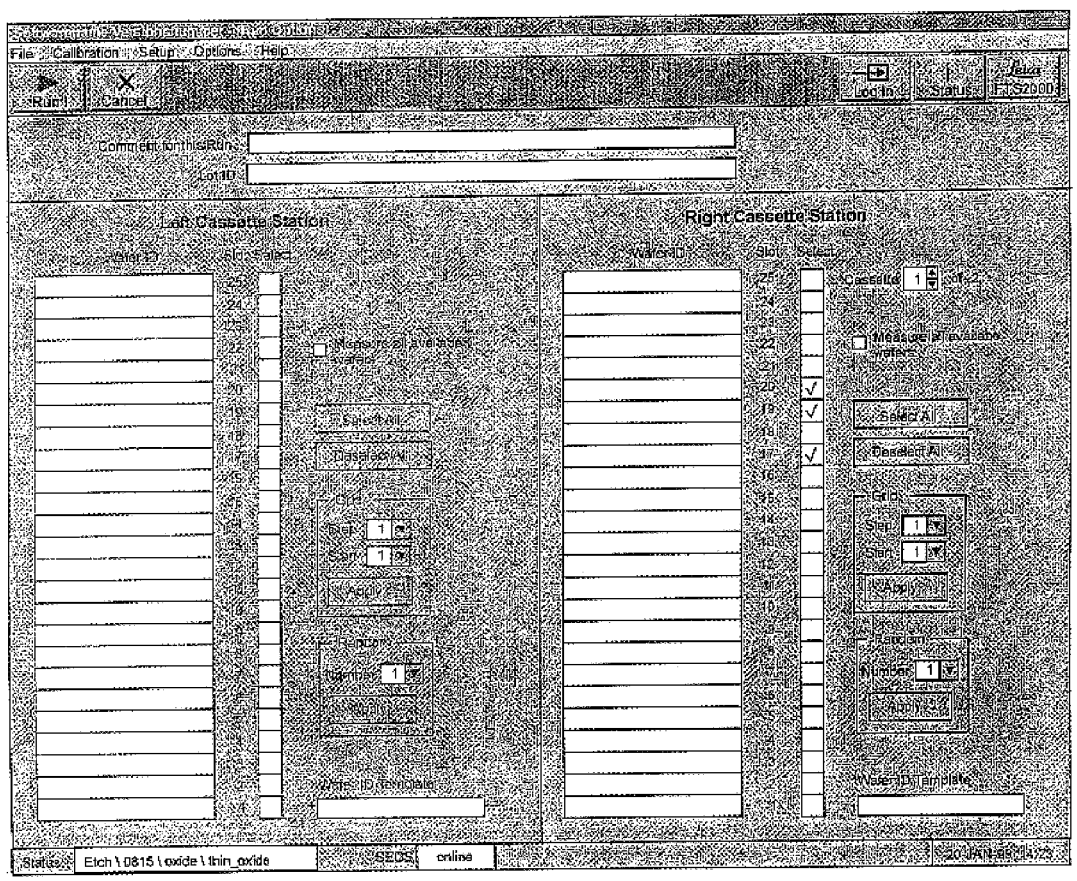
FIGS. 17 and 18 are schematic drawings of the details of an inspection or measurement run ("run")
Figure 18:
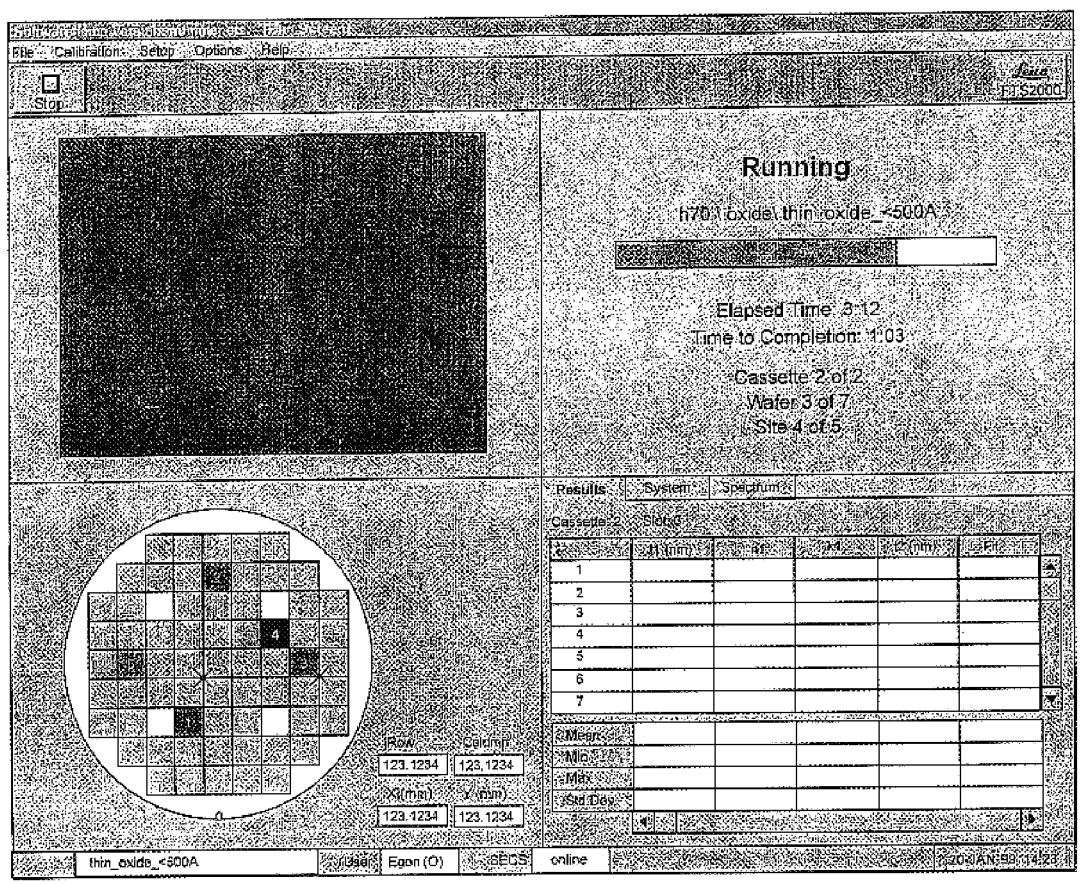
Figure 19:
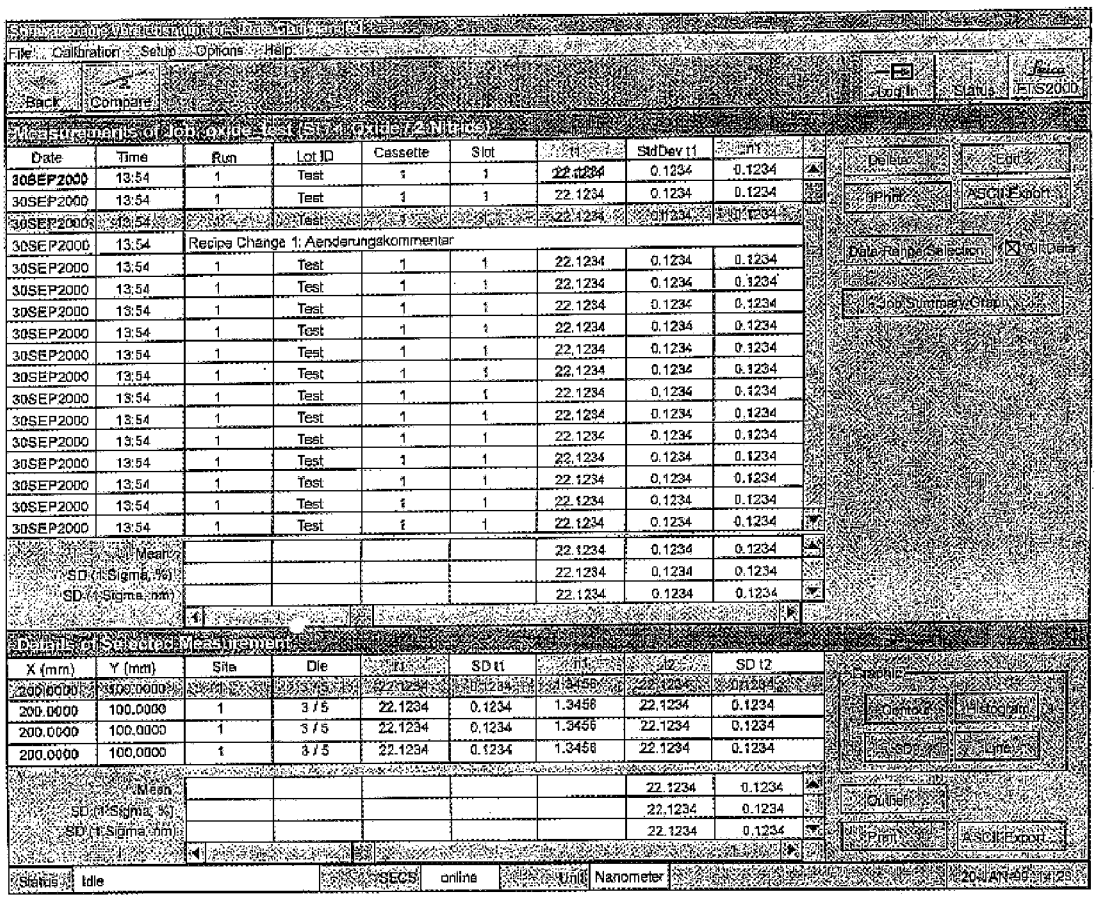
FIGS. 19 to 21 are schematic drawings of the details of the data commander.
Figure 20:
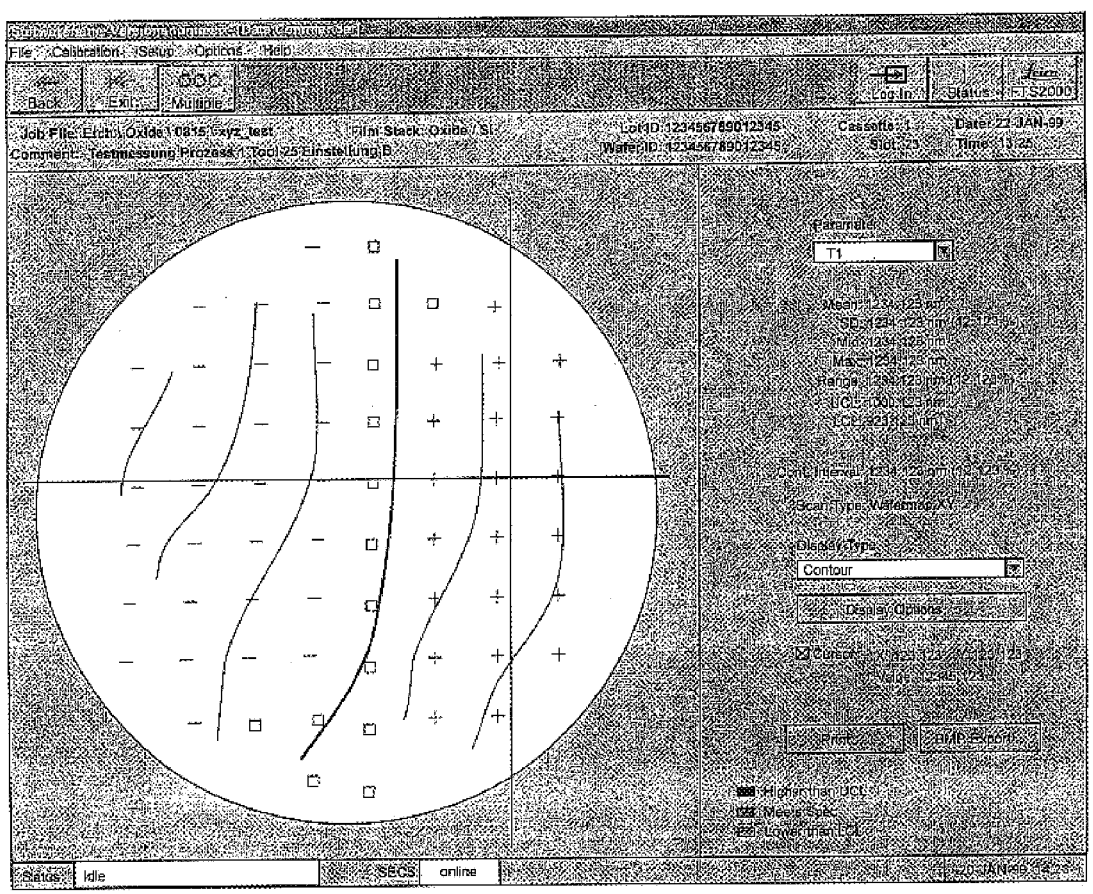
Figure 21:
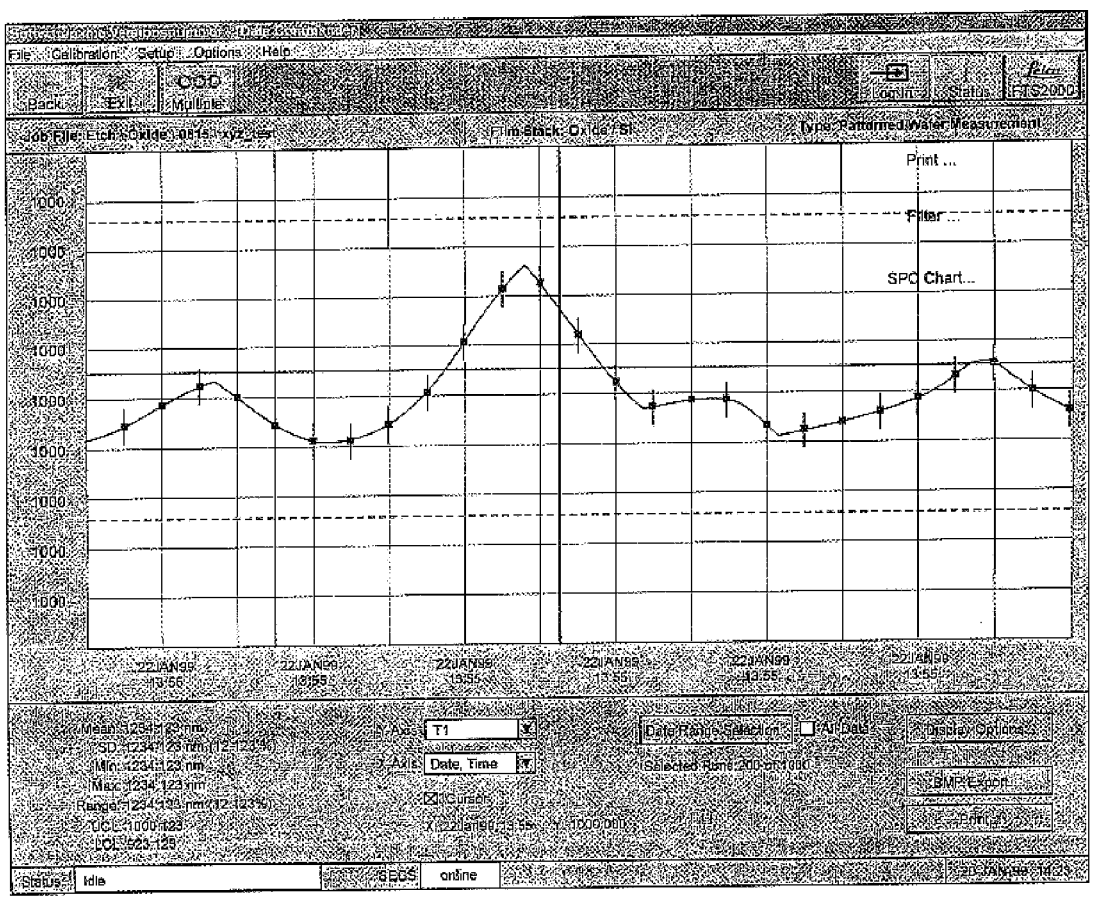
Figure 22:
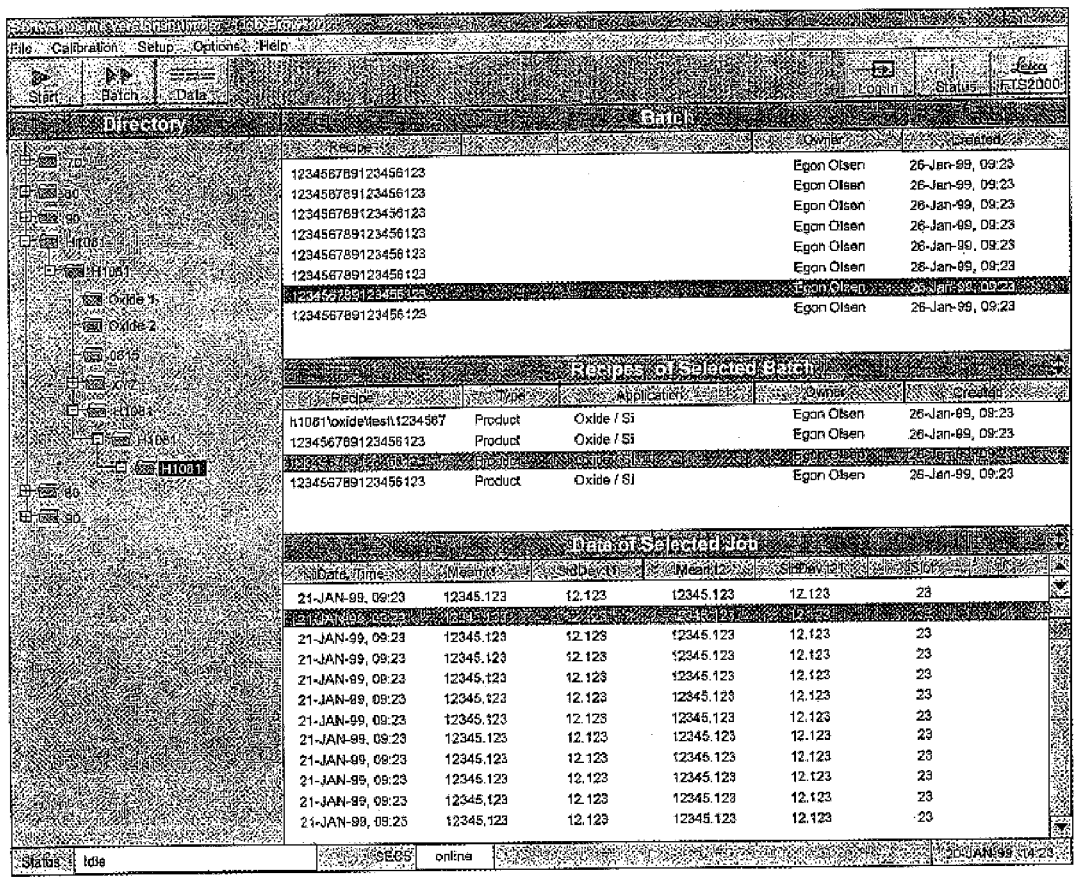
FIG. 22 is a schematic drawing of the browser for batch jobs.

In the context of the above explanations, FIGS. 10 to 22 are self explanatory owing to their labeling. FIGS. 10 to 16 give details about the job commander. Details about the measurement run ("run") are in FIGS. 17 and 18; details about the data commander, in FIGS. 19 to 21; and about the batch jobs, in FIG. 22.

FIG. 23 shows as an example of the state of the art a screen mask, where an arrow 20 can be moved up and down by means of a cursor key on a keyboard. If the arrow points to a specific menu point (key word, e.g. "material catalogue"), the corresponding program is executed or changed to the related screen mask.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. In an optical measurement system for inspecting and measuring coated and non-coated substrates, the improvement comprising: a user guidance apparatus for guiding a user through the optical inspection and measurement of the coated and non-coated substrates, wherein the user guidance apparatus, comprises:

a user interface coupled with the optical measurement system; and wherein the user interface comprises an integrated measurement recipe and data browser having sortable fields providing simultaneous access and display of the measurement recipe and data browser to the user.

2. The optical measurement system according to claim 1, wherein the user interface further comprises a directory tree, in which directories with data for the integrated measurement recipe and data browser are opened or set-up, said directory tree appearing simultaneously with the integrated measurement recipe and data browser in the user interface, and being operable simultaneously.

3. The optical measurement system according to claim 2, wherein the directory tree and the integrated measurement recipe and data browser are provided on a computer display screen.

4. The optical measurement system according to claim 1, further comprising an interactive, storable research measurement unit, wherein during a recipe set-up, the interactive, storable research measurement unit is executable to incorporate current setting values into a current recipe being set-up.

5. The optical measurement system according to claim 2, further comprising an interactive, storable research measurement unit, wherein during a recipe set-up, the interactive, storable research measurement unit is executable to incorporate current setting values into a current recipe being set-up.

6. The optical measurement system according to claim 3, further comprising an interactive, storable research measurement unit, wherein during a recipe set-up, the interactive, storable research measurement unit is executable to incorporate current setting values into a current recipe being set-up.

7. The optical measurement system according to claim 1, wherein the user interface further comprises a job commander for detailed input of parameters of a particular job.

8. The optical measurement system according to claim 2, wherein the user interface further comprises a job commander for detailed input of parameters of a particular job.

9. The optical measurement system according to claim 1, wherein the user interface further comprises a data commander for detailed display of inspection and measurement results.

10. The optical measurement system according to claim 2, wherein the user interface further comprises a data commander for detailed display of inspection and measurement results.

11. The optical measurement system according to claim 1, wherein the optical measurement system is a layer analysis system.

12. The optical measurement system according to claim 11, wherein the layer analysis system includes a spectrophotometer and a spectroellipsometer.

13. The optical measurement system according to claim 11, wherein the apparatus links two types of measurements made by the layer analysis system.

14. The optical measurement system according to claim 12, wherein measurements of the spectrophotometer and the spectroellipsometer are linked together during a layer analysis process by the apparatus.

15. In an optical measurement system for inspecting and measuring coated and non-coated substrates, the improvement comprising:

a computer readable medium having stored thereon program code for guiding users during optical inspection and measurement of coated and non-coated substrates via the optical measurement system, said program code comprising an integrated measurement recipe and data browser having sortable fields providing simultaneous access and display of the measurement recipe and data browser to the user.

16. The optical measurement system according to claim 15, wherein said program code further comprises a directory tree, in which directories having data for the integrated measurement recipe and data browser are opened or set-up, said directory tree appearing simultaneously with the integrated measurement recipe and data browser in a user interface so as to be operable simultaneously.

17. The optical measurement system according to claim 15, wherein the program code incorporates recipe set-up code by which an interactive, storable research measurement unit incorporates current setting values into a current recipe.

18. A method of operating an optical measurement system for inspecting and measuring coated and non-coated substrates, the method comprising the acts of:

displaying a user interface incorporating an integrated measurement recipe and data browser having sortable fields providing simultaneous access and display of the measurement recipe and data browser to the user; and selecting at least one of an inspection and measurement task via the integrated measurement recipe and data browser.

19. The method according to claim 18, further comprising the act of simultaneously displaying a directory tree with the integrated measurement recipe and data browser; and opening or setting-up a directory that contains data for the integrated measurement recipe and data browser, said directory tree being operable simultaneously with the integrated measurement recipe and data browser.

* * * * *